United States Patent [19]

Wu et al.

[11] 4,173,587

[45] Nov. 6, 1979

[54] DECOMPOSITION OF CUMENE HYDROPEROXIDE WITH A HETEROGENEOUS CATALYST

[75] Inventors: Ching-Yong Wu, O'Hara Township, Allegheny County; Wayne R. Pretzer, Oakmont; Thaddeus P. Kobylinski, Gibsonia, all of Pa.

[73] Assignee: Gulf Research and Development Company, Pittsburgh, Pa.

[21] Appl. No.: 852,922

[22] Filed: Nov. 18, 1977

[51] Int. Cl.$^2$ .................... C07C 49/08; C07C 39/04; C07C 37/08; C07C 45/00

[52] U.S. Cl. ................................ 260/593 A; 568/798
[58] Field of Search .................... 260/593 A; 568/798

[56] References Cited

FOREIGN PATENT DOCUMENTS 5180830 7/1976 Japan.

Primary Examiner—Joseph E. Evans

[57] ABSTRACT

Cumene hydroperoxide in a solvent is decomposed to phenol and acetone using a non-soluble rhenium compound.

11 Claims, No Drawings

DECOMPOSITION OF CUMENE HYDROPEROXIDE WITH A HETEROGENEOUS CATALYST

FIELD OF THE INVENTION

This invention relates to the catalytic cleavage of cumene hydroperoxide to equal molar portions of phenol and acetone.

DESCRIPTION OF THE PRIOR ART

Cumene can be readily oxidized with air to form cumene hydroperoxide and the hydroperoxide can then be decomposed to form equal molar amounts of phenol and acetone. In the commercial process for producing phenol by this general method, a dilute solution of a mineral acid, generally sulfuric acid, is used as the decomposition or cleavage catalyst. Since phenol and acetone are the products of the cleavage reaction, the reaction solvent can conveniently be a phenol-acetone solution. In this process the cumene hydroperoxide instantaneously decomposes to phenol and acetone as it is slowly added in solution with cumene to the mineral acid solution. The highly exothermic reaction is controlled by the rate of cumene hdroperoxide addition and by acetone reflux. Water is substantially excluded from the reaction mixture to insure homogeneity. These processing details are essentially described in U.S. Pat. No. 2,663,735.

U.S. Pat. No. 3,351,635, relating to the epoxidation of olefins using hydroperoxides, such as cumene hydroperoxide, discloses in Example 15 that rhenium heptoxide dissolved in the reaction mixture catalyzes the decomposition of hydroperoxide with 80 percent yield to decomposition products. This teaching that rhenium heptoxide is a hydroperoxide decomposition catalyst is covered in Japanese application No. 51-80830, published July 15, 1976. In this published application rhenium heptoxide is specified as a catalyst for the decomposition of cumene hydroperoxide in an inert solvent. Phenol and phenol-acetone mixtures are excluded as a solvent component. The decomposition of cumene hydroperoxide is described by the Japanese application as taking 30 minutes to complete at about 100° C. in contrast to the substantially instantaneous decomposition of the acid-catalyzed commercial processes, but advantageously, this rhenium catalyzed process, as described, produces a phenol-acetone mixture with less undesirable impurities including less tar-like impurities than the acid-catalyzed processes.

Since the rhenium heptoxide readily dissolves in the reaction liquid forming a homogeneous reaction system, its use presents a special problem. That is, the costly rhenium represents a substantial economic loss if it is discarded after recovery of the reaction product. On the other hand, it is a substantial economic burden to recover, purify and reactivate this costly rhenium catalyst.

SUMMARY OF THE INVENTION

We have discovered that cumene hydroperoxide can be cleaved in high yield to phenol and acetone by the use of a solid, substantially non-soluble rhenium catalyst. As part of our invention we have discovered that a rhenium compound supported on an inert support such as alumina is highly active for the decomposition of cumene hydroperoxide to phenol and acetone. Since the rhenium will not leach out from the supported catalyst during the decomposition reaction, it retains its catalytic activity for a long period of time. We have further discovered that treatment of the support with an alkali metal or alkaline earth metal compound significantly improves the reaction selectivity to phenol and that sulfiding the supported rhenium catalyst effectively improves the activity of the catalyst. This supported catalyst can be used as a powder suspended in the reaction liquid or in the form of pellets, such as one to five millimeters in size, in a stationary bed. We have also discovered that cumene hydroperoxide can be cleaved to phenol and acetone in high yield in a heterogeneous system using a non-soluble, unsupported compound of rhenium such as rhenium heptasulfide.

The supported catalyst of our invention can be prepared by impregnating the support with a solution of a rhenium compound, followed by drying and calcining the impregnated support. For example, a solution of rhenium heptoxide or ammonium perrhenate in water can be introduced into alumina by impregnation. The concentration of the rhenium in the solution and the amount of the solution is adjusted to obtain a supported catalyst containing from about one percent to about 25 percent rhenium determined as the metal. However, it is preferred that the catalyst contain from about 5 to about 20 percent of the rhenium determined as the metal.

The preferred support is alumina, however, certain other solids can be used as a support such as zirconia, silica-alumina or alumina-magnesia containing at least about 10 weight percent alumina, preferably at least about 25 percent alumina, and the like. Certain support-type materials are not useful. For example, if silica is used as the support, there is severe leaching of rhenium from the support. When carbon or silicon-carbide is used, the selectivity to phenol is undesirably low.

We have found, as stated, that the supported rhenium catalyst of our invention can be made more selective if the support is treated with an alkali metal or alkaline earth metal compound prior to the addition of rhenium to the support. Sodium and potassium are the preferred alkali metals and calcium, strontium and barium are the preferred alkaline earth metals with magnesium being less desirable because of a tendency to leach from the support. The support can be impregnated with an aqueous solution of the alkali metal or alkali metal compounds, such as the hydroxide, carbonate, bicarbonate and the like, then dried and calcined. The amount of the alkali metal or alkaline earth metal that is incorporated into the support is up to about five percent metal based on the final catalyst, preferably about 0.5 to about 2.5 percent metal. Following this treatment, the rhenium can then be incorporated on the support. However, the support can also be successfully treated with the alkali or alkaline earth metal concurrently with or subsequent to the treatment with the rhenium compound. The support can conveniently be dried after both the alkali or alkaline earth metal impregnating step and the rhenium impregnating step at a temperature between about 100° and about 200° C. and calcined at a temperature between about 200° and about 450° C.

The supported rhenium catalyst can be sulfided to substantially increase its activity as measured by the time required for complete decomposition of the cumene hydroperoxide. This sulfiding can be successfully carried out on the rhenium catalyst either with or without the alkali metal or alkaline earth metal pretreatment. This sulfiding can be effectively performed by subjecting the supported rhenium catalyst to a gaseous sulfur compound such as hydrogen sulfide at a temperature of between about 15° C. and about 450° C. until substantial reaction has occurred as determined by substantial blackening of the catalyst. The sulfiding treatment can be effectively carried out for a time ranging from 10 minutes to 24 hours, whereby a substantial portion, preferably all, of the rhenium is converted to one or more rhenium sulfides.

The catalyst that we can use in our heterogeneous process can also be a substantially non-soluble, unsupported compound of rhenium such as rhenium heptasulfide or other rhenium sulfides. These non-soluble rhenium compounds can be successfully used by suspending the rhenium compound in particulate form in the reaction fluid such as by agitation. These non-soluble rhenium compounds can also be embedded in a matrix of an inert material such as alumina, zirconia, silica-alumina or magnesia-alumina in which there is at least about ten percent alumina, preferably at least about 25 percent alumina, and the like. When the rhenium compound is embedded in a matrix, at least about one weight percent of the rhenium compound is used, preferably at least about ten weight percent. This embedded catalyst can also be used as a suspension of fine particles or it can be formed into pellets for use in a stationary catalyst bed.

The desired decomposition of the cumene hydroperoxide is a cleavage to equal mols of phenol and acetone, that is, about 62 weight percent phenol and 38 weight percent acetone. In using sulfuric acid as the decomposition catalyst, a selectivity to phenol of about 85 to 95 percent is generally obtained. The non-selective decomposition product particularly as catalyzed by a strong mineral acid includes cumyl alcohol, acetophenone, methyl benzofuran, organic acids, cumyl phenols, alpha-methylstyrene and various oligomers of alpha-methylstyrene which are tar-like substances. Since few of these by-products of the non-selective reaction can be economically recovered, this non-selective reaction represents a significant economic loss.

A particular advantage in the use of the rhenium catalyst is that a selectivity greater than 90 percent, approaching 100 percent under optimum conditions, can be obtained. Another advantage of the rhenium catalyst in contrast with the strong mineral acid catalyst is that the rhenium catalyst is a non-acidic catalyst which does not promote the alkylation of phenol product to cumyl phenol nor the oligomerization of aromatic olefin to form tars. Furthermore, in the rhenium catalyzed reaction the major by-product, alpha-methylstyrene, is recovered and hydrogenated to cumene for recycle in the process. A further advantage in the use of the rhenium catalyst instead of the mineral acid is that the corrosion problems, neutralization procedures and the waste handling problems of the latter are substantially avoided. A particular advantage in the use of a phenol-acetone mixture as the reaction solvent is that final separation is simplified since phenol and acetone are also the product of the decomposition.

The cumene hydroperoxide can desirably be prepared by the air oxidation of cumene in the conventional manner. In this process a solution of about 10 to 30 percent cumene hydroperoxide in cumene is produced. This product can be used as the feed to the cleavage reactor with the cumene serving as a solvent for the cumene hydroperoxide. If another solvent is desired, the cumene hydroperoxide can be obtained by flashing off sufficient cumene to form a solution of between about 60 to about 90 percent, preferably about 65 to about 80 percent, cumene hydroperoxide. Although pure cumene hydroperoxide can be separated out, it is less desirable to obtain it in this final stage of purity for economic reasons and also for safety reasons, since the presence of some cumene tends to stabilize the cumene hydroperoxide.

This concentrated cumene hydroperoxide can then be added to a second solvent. Suitable solvents include a solvent or solvent mixture selected from aromatic hydrocarbons having from six to about ten carbon atoms such as benzene, toluene, ethylbenzene, xylene, and the like; alkyl hydrocarbons having from about five to about ten carbon atoms such as pentane, hexane, cyclohexane, heptane, and the like, and ketones having from three to about ten carbon atoms such as acetone, methyl ethyl ketone, and the like. Since a phenol-acetone mixture is the product of the decomposition, this is the preferred solvent in order to minimize separation problems following the reaction. A mol ratio of phenol to acetone of between about 1:1 to about 1:10, preferably between about 1:1 and about 1:3, can conveniently be used in the reaction liquid.

Sufficient solvent is used to provide a suitable concentration of the cumene hydroperoxide for the decomposition reaction. The decomposition reaction can suitably be carried out with as little as about 0.1 weight percent cumene hydroperoxide in the reaction liquid, with at least about 0.5 percent being preferred and at least about 1.0 percent being most preferred. The maximum amount of cumene hydroperoxide in the cleavage reaction liquid will be about 20 weight percent, preferably about 10 percent and most preferably about 5 percent.

We have discovered as one aspect of our invention that phenol can be used as a reaction solvent for the relatively slow rhenium catalyzed reaction. This is quite surprising because phenol, by virtue of its acid nature, has been found to be a catalyst for the decomposition of cumene hydroperoxide. This phenol catalyzed decomposition is significantly slower than the above-described mineral acid catalyzed reaction. Moreover, the selectivity of this phenol catalyzed decomposition of cumene hydroperoxide is very poor, being less than 80 percent selectivity to phenol as determined by our study of the reaction. It is readily apparent that the presence of solvent phenol in the mineral acid catalyzed reaction of the commercial processes is not noticeably detrimental because the great speed of the mineral acid catalyzed decomposition effectively eliminates the detrimental effect on selectivity of the relatively slow phenol catalyzed reaction. However, the obvious undesirability of the presence of phenol as a solvent for the reaction mixture for the relatively slow rhenium-catalyzed decomposition reaction is suggested by its exclusion as a solvent in the published Japanese application which requires an inert solvent.

Notwithstanding this detrimental effect of phenol on the decomposition of cumene hydroperoxide, we have surprisingly discovered in accordance with this aspect of our invention that phenol, and more particularly a mixture of phenol and acetone, can be effectively used as a reaction medium for the decomposition of cumene hydroperoxide using a heterogeneous rhenium catalyst. In our process the decomposition reaction proceeds with very high selectivity to phenol and acetone, even substantially higher selectivity than resulting from mineral acid catalyzed decompositions. According to our discovery, we have found that the non-selective phenol catalyzed decomposition of cumene hydroperoxide can be minimized while retaining a substantial rate of the highly selective rhenium-catalyzed cleavage of the cumene hydroperoxide by careful control of the reaction conditions within critical limits. Furthermore, we have found that these reaction conditions are such that they advantageously permit the operation of this novel process in existing cumene-to-phenol commercial plants.

This aspect of our invention is based, in part, on the discovery that the phenol catalyzed decomposition reaction is significantly more temperature dependent than the rhenium catalyzed decomposition reaction. That is, as the temperature is lowered, other conditions remaining the same, the rate of the phenol catalyzed decomposition drops much more rapidly than the rate of the rhenium catalyzed reaction permitting the cumene hydroperoxide to selectively decompose to phenol and acetone. We have found, in particular, that by a careful correlation of the cleavage reaction temperature and the time of reaction, a suitable rate of cleavage of the cumene hydroperoxide can be maintained with minimum decomposition to undesired products.

If a temperature much in excess of 80° C. is utilized for the decomposition reaction when phenol is used as a solvent for the cumene hydroperoxide, then the undesirable phenol catalyzed reaction tends to become excessive. Therefore, a maximum reaction temperature of about 80° C. is used, more preferably a maximum temperature of about 70° C. and most preferably a maximum temperature of about 65° C. A minimum temperature of at least about 40° C. has been found necessary to obtain a suitable rate of the desired cleavage reaction while a minimum temperature of at least about 50° C. is more preferred and a minimum temperature of at least about 55° C. is most preferred.

Our decomposition process can be carried out as either a batch or a continuous process in which the catalyst in fine particulate form is suspended in the liquid undergoing decomposition for sufficient time to obtain substantially complete decomposition at the reaction temperature. In using this procedure we have also found it desirable to carry out the decomposition reaction at an average catalyst contact time of from about one to about 60 minutes, preferably about 5 to about 40 minutes and most preferably between about 10 to about 25 minutes for substantially complete decomposition and high selectivity.

Preferably, however, the process is carried out by placing the catalyst in the form of pellets or other conventional form in a fixed bed and passing the cumene hydroperoxide solution through the catalyst bed. The reaction can be suitably carried out if the cumene hydroperoxide solution is passed over the catalyst at a liquid hourly space velocity of between about one and about 20,000, preferably about 3 to about 10,000. The space velocity is, in part, dependent on the concentration of rhenium in the catalyst and on the reaction temperature, since the reaction rate is very significantly affected by temperature. A temperature of between about 10° and about 150° C. can be successfully used when phenol is not used as a solvent. However, we prefer a range when the supported catalyst is used of between about 40° and about 125° C. and more preferably between about 70° and about 110° C. and when the non-supported catalyst is used, a temperature between about 30° and about 100° C. is preferred and a temperature between about 55° and 75° C. is most preferred. The pressure within the reactor is not a critical factor during the decomposition reaction. Generally, the pressure will range from a pressure moderately below to moderately above atmospheric pressure.

DESCRIPTION OF PREFERRED EMBODIMENTS

EXAMPLE 1

The catalytic activity of sulfuric acid for the decomposition of cumene hydroperoxide was observed. A 57.3 percent solution of cumene hydroperoxide in cumene was added dropwise into 100 ml. of a two percent solution of sulfuric acid in acetone in a 300 ml. round bottom flask open to the atmosphere. Each drop instantly decomposed as it contacted the solution. Since no positive cooling of the reaction liquid was provided, the temperature of the solution rose from room temperature (about 25° C.) at the beginning of the addition to 44° C. upon the completion of the addition. A total of 35.2 g. of the cumene hydroperoxide was added over 60 minutes. Analysis of the very dark colored product showed that 99.9 percent of the cumene hydroperoxide had reacted at a selectivity of 93 percent to phenol with tars, cumyl phenol and mesityl oxide being major by-products.

The reactions described in the following examples were carried out in a glass reactor equipped with a magnetic stirrer operated at ambient pressure within the reactor slightly above atmospheric pressure. The reactor was cooled by a cold finger in the liquid. Small samples of the reaction liquid (about 1 ml.) were periodically withdrawn to monitor the reaction. The product was analyzed by titration for active oxygen, by gas chromatography and by high performance liquid chromatography.

EXAMPLE 2

Phenol was tested as a decomposition catalyst for cumene hydroperoxide at several temperatures. About 20 g. of a solution consisting of 5 parts phenol, 3 parts acetone and one part cumene were placed in the reactor. About 2 ml. of a solution consisting of 55 percent cumene hydroperoxide in cumene were injected into the reactor in each experiment. Table I summarizes the results of these experiments.

Table I

| Minutes Temp. | Cumene Hydroperoxide Decomposed, % | | | |
|---|---|---|---|---|
| | 10 | 20 | 50 | 100 |
| 40° C. | trace | trace | trace | trace |
| 60° C. | — | 8 | 19 | 39 |
| 80° C. | 18 | 34 | 60 | 85 |

The experiment at 80° C. was allowed to run for four and one-half hours at which time the cumene hydroperoxide was completely decomposed. Analysis of this product mixture disclosed that it contained 77 percent phenol, 8 percent alpha-methylstyrene, 4 percent acetophenone, 4 percent dimethylbenzyl alcohol, and 7 percent of a residuum consisting of aromatic carbonyls, aromatic alcohols, substituted phenols, substituted benzofurans and methylstyrene oligomers.

EXAMPLE 3

This experiment was carried out to determine the catalytic activity of alumina in the decomposition of cumene hydroperoxide. The glass reactor was charged with 22 g. of a solution of 23.0 percent cumene hydroperoxide in cumene and 0.030 g. of powdered alpha-alumina. The contents were heated at 105° C. for two hours. Titration of the solution showed 21.9 percent cumene hydroperoxide which indicated less than five percent decomposition of the cumene hydroperoxide.

EXAMPLE 4

Rhenium was impregnated on alumina by the technique of incipient wetness. Accordingly, 0.13 g. rhenium heptoxide was dissolved in that amount of water necessary to just fill the pore space of 0.40 g. of alpha-$Al_2O_3$ (surface area 200–250 $m^2/g$) and the resulting solution used to treat 0.40 g. of the alumina. After 30 minutes the treated alumina was washed once with water, dried in vacuo for 12 hours at 150° C., and calcined in air at 500° C. for two hours. Analysis of the calcined powdered product showed the rhenium heptoxide content to be 10 percent, not 20 percent. Calcining at 500° C. evidently leads to loss of rhenium heptoxide and subsequent experiments have shown that simple drying at 150° C. is satisfactory.

To 22.0 g. of 19.2 percent cumene hydroperoxide in cumene in the stirred glass reactor was added 0.025 g. of the above prepared catalyst. The mixture was heated to 105°–110° C. for 30 minutes during which time over 94 percent of the cumene hydroperoxide decomposed affording an 88 percent yield of phenol. The major by-product was alpha-methylstyrene. The product solution was pale yellow and tar formation was very slight.

EXAMPLE 5

In order to show the improved performance of alkali metal treated alumina, 0.80 g. of alumina was treated with 0.020 g. of potassium hydroxide in sufficient water to just wet the alumina. The material was dried in one hour in vacuo at 150° C. and then treated with 0.260 g. of rhenium heptoxide in sufficient water to wet the alumina. The treated alumina was dried in vacuo at 150° C. for 12 hours and calcined at 500° C. in air for two hours. Analysis of the powdered product showed 10 percent rhenium heptoxide by weight.

A 22.0 g. solution of 19.8 percent cumene hydroperoxide in cumene and 0.028 g. of the Re-K-$Al_2O_3$ catalyst were placed into a glass reactor equipped with a magnetic stirrer. The contents were heated to 105°–115° C. for 50 minutes during which time over 99 percent of the cumene hydroperoxide decomposed with a phenol yield of 95 percent. The major by-product was alpha-methylstyrene in 4 percent yield. The product solution was yellow and tar formation was nil.

EXAMPLE 6

In this example the catalyst is tested for activity after repeated reuse. Into a stirred glass reactor was placed 0.030 g. of another portion of the Re-K-$Al_2O_3$ catalyst as prepared in Example 5. The reactor was charged with 22.0 g. of a solution of 22.5 percent cumene hydroperoxide in cumene solution and the contents heated for 1.5 hours at 105° C. During this time, greater than 99 percent of the cumene hydroperoxide decomposed with a selectivity to phenol of 92 percent and 5 percent of alpha-methylstyrene. Tar formation was nil.

The light yellow product solution was decanted and a fresh 22.7 percent solution of cumene hydroperoxide in cumene was charged into the reactor. After heating at 105° C. for 1.5 hours, greater than 99 percent of the cumene hydroperoxide decomposed to phenol in 93 percent yield and alpha-methylstyrene in 6 percent yield. Tar formation was slight.

After decanting the product solution, a third fresh charge of 21.9 percent cumene hydroperoxide in cumene was completely decomposed after two hours at 105° C. Phenol selectivity was 92 percent and alpha-methylstyrene was the major by-product at 7 percent yield. Tar formation was negligible.

EXAMPLE 7

In order to demonstrate the activity of a sulfided catalyst, 800 mg. of a 14 percent rhenium heptoxide on alumina catalyst were prepared by treating alumina with an appropriate amount of $NH_4ReO_4$ dissolved in water, drying at 150° C. for two hours, and calcining at 400° C. for two hours. This powdered catalyst was treated with a 1:1 mixture of nitrogen and hydrogen sulfide for two hours at 130° C. during which time the catalyst blackened considerably.

A 0.004 g. portion of the above sulfided catalyst was placed in the glass reactor with 4.0 g. of a 20 percent solution of cumene hydroperoxide in cumene and the contents were heated to 80° C. After 30 minutes greater than 99 percent of the cumene hydroperoxide had decomposed to phenol and acetone. The product was decanted and a fresh 20 percent solution of cumene hydroperoxide in cumene was charged into the reactor. After 60 minutes at 80° C. greater than 99 percent cumene hydroperoxide decomposition to phenol and acetone was observed. The product was again decanted, and a third cumene hydroperoxide charge was put into the reactor. After 60 minutes at 80° C., greater than 99 percent of the cumene hydroperoxide had decomposed to phenol and acetone. In all cases tar formation was negligible.

A 0.004 g. portion of the non-sulfided 14 percent rhenium heptoxide on alumina catalyst was placed in the reactor with 4.0 g. of a 20 percent solution of cumene hydroperoxide in cumene. After 30 minutes at 80° C., 10 percent of the cumene hydroperoxide had decomposed to phenol and acetone; and after 60 minutes at 80° C., 75 percent of the cumene hydroperoxide had decomposed. The increased activity of the sulfided catalyst was evident.

EXAMPLE 8

A catalyst was prepared having 5 percent rhenium supported on carbon. A 0.105 g. portion of this catalyst was placed in a stirred glass reactor with 22 g. of a 19.1 percent solution of cumene hydroperoxide in cumene and was heated to 85°–95° C. for 45 minutes. During this time less than 15 percent of the cumene hydroperoxide decomposed. The contents were further heated for an additional 50 minutes at 100°–126° C. More than 95 percent of the cumene hydroperoxide decomposed, but the yield of phenol was only 49 percent. The major by-product was alpha-methylstyrene in 24 percent yield.

EXAMPLE 9

A 0.012 g. portion of a rhenium wire was placed in the stirred glass reactor with 22.0 g. of a 19.5 percent solution of cumene hydroperoxide in cumene. The contents were heated for 50 minutes at 80° C. No decomposition occurred. The contents were then heated to 106°–118° C. for 50 minutes during which time 62 percent of the cumene hydroperoxide decomposed with a phenol yield of 82 percent. Leaching of rhenium was suggested since upon removal of the wire and continued heating for 50 minutes at 106° C., complete cumene hydroperoxide decomposition was observed.

EXAMPLE 10

In order to determine the effect of reduced rhenium content, 0.14 g. of rhenium heptoxide was dissolved in 10 ml. of water and then used to treat 10.0 g. of alumina. The treated alumina was dried in vacuo at 150° C. for 12 hours and then calcined in air at 500° C. for 6 hours. Analysis showed one percent rhenium heptoxide by weight. A 0.525 g. portion of the above produced rhenium heptoxide on alumina catalyst was placed in the stirred glass reactor with 22.0 g. of a 16 percent solution of cumene hydroperoxide in cumene and heated to 115° C. for 40 minutes. Only 14 percent of the cumene hydroperoxide decomposed during this time.

EXAMPLE 11

A 0.009 g. portion of powdered rhenium heptasulfide was placed in a stirred glass reactor with 22 g. of a 17.4 percent solution of cumene hydroperoxide in cumene and heated to 60°–105° C. for five minutes. The catalyst did not appear to dissolve. Cumene hydroperoxide decomposition was complete and phenol yield was greater than 92 percent. The major by-product was alpha-methylstyrene in 6 percent yield with tar formation being nil.

EXAMPLE 12

A 0.002 g. sample of powdered rhenium heptasulfide was placed in a stirred glass reactor. A 22.0 g. portion of a solution consisting of five percent by weight cumene hydroperoxide, 15 percent cumene, 30 percent acetone, and 50 percent phenol was charged into the reactor. The contents were heated to 60° C. for 100 minutes during which time the cumene hydroperoxide was completely decomposed to phenol and acetone.

EXAMPLE 13

A 0.010 g. sample of powdered rhenium trioxide was placed in a stirred glass reactor with 22 g. of a 17.4 percent solution of cumene hydroperoxide in cumene and was heated to 60°–115° C. for five minutes. The catalyst was insoluble. Decomposition of the cumene hydroperoxide was complete and the phenol yield was greater than 92 percent. The major by-product was alpha-methylstyrene in six percent yield with tar formation being negligible.

It is to be understood that the above disclosure is by way of specific example and that numerous modifications and variations are available to those of ordinary skill in the art without departing from the true spirit and scope of the invention.

We claim:

1. The method for cleaving cumene hydroperoxide at high selectivity to phenol and acetone using a heterogeneous rhenium catalyst which comprises heating a solution comprising about 0.1 to about 20 weight percent cumene hydroperoxide in a solvent in the presence of a rhenium catalyst consisting essentially of a substantially non-soluble rhenium compound selected from unsupported rhenium sulfides, calcined supported rhenium oxides and sulfided supported rhenium oxides wherein said supports are selected from alumina, zirconia and a silica-alumina or a magnesia-alumina having at least about ten weight percent alumina at a temperature between about 10° C. and about 150° C.

2. The method in accordance with claim 1 in which the supported rhenium oxide is calcined at a temperature between about 200° C. and about 450° C.

3. The method in accordance with claim 1 in which the support has been treated to contain up to about 5 weight percent of an alkali or alkaline earth metal.

4. The method in accordance with claim 1 in which the solvent is an inert solvent selected from aromatic hydrocarbons having up to about ten carbon atoms, alkyl hydrocarbons having up to about ten carbon atoms and ketones having between about three and ten carbon atoms.

5. The method in accordance with claim 1 in which the unsupported rhenium sulfide is admixed with up to about 99 percent of an inert matrix selected from alumina, zirconia and a silica-alumina or a magnesia-alumina having at least about 10 weight percent alumina.

6. The method in accordance with claim 1 in which said solution comprises between about 0.5 and about 10 weight percent cumene hydroperoxide.

7. The method in accordance with claim 1 in which said solution comprises between about one and about five weight percent cumene hydroperoxide.

8. The method in accordance with claim 1 in which the temperature is between about 40° and about 110° C.

9. The method in accordance with claim 1 in which the supported catalyst contains from about one to about 25 weight percent rhenium determined as the metal.

10. The method in accordance with claim 1 in which the supported catalyst contains from about five to about 20 weight percent rhenium determined as the metal.

11. The method in accordance with claim 1 in which the unsupported rhenium sulfide is rhenium heptasulfide.

* * * * *